(12) United States Patent
Feiweier et al.

(10) Patent No.: US 10,185,890 B2
(45) Date of Patent: Jan. 22, 2019

(54) METHOD, COMPUTER AND IMAGING APPARATUS FOR EVALUATING MEDICAL IMAGE DATA OF AN EXAMINATION SUBJECT

(71) Applicant: Siemens Healthcare GmbH, Erlangen (DE)

(72) Inventors: Thorsten Feiweier, Poxdorf (DE); Oliver Patrick Welzel, Speichersdorf (DE)

(73) Assignee: Siemens Healthcare GmbH, Erlangen (DE)

(*) Notice: Subject to any disclaimer, the term of this patent is extended or adjusted under 35 U.S.C. 154(b) by 111 days.

(21) Appl. No.: 15/343,552

(22) Filed: Nov. 4, 2016

(65) Prior Publication Data
US 2017/0132491 A1 May 11, 2017

(30) Foreign Application Priority Data
Nov. 6, 2015 (DE) .................. 10 2015 221 876

(51) Int. Cl.
*G06K 9/62* (2006.01)
*A61B 5/00* (2006.01)
(Continued)

(52) U.S. Cl.
CPC .......... *G06K 9/6202* (2013.01); *A61B 5/0042* (2013.01); *A61B 5/055* (2013.01); *A61B 5/4088* (2013.01); *A61B 5/72* (2013.01); *A61B 6/032* (2013.01); *A61B 6/037* (2013.01); *A61B 8/00* (2013.01); *G06T 7/0079* (2013.01); *G06T 2207/30016* (2013.01); *G06T 2207/30204* (2013.01)

(58) Field of Classification Search
USPC ........................................ 382/128
See application file for complete search history.

(56) References Cited

U.S. PATENT DOCUMENTS 9,504,428 B1  11/2016  Gelbman et al.
2005/0256397 A1* 11/2005  De Leon ............ A61B 5/055
                                                600/420
(Continued)

OTHER PUBLICATIONS

Stein et al, "Identification of common variants associated with human hippocampal and intracranial volume", Nature Genetics, vol. 44, p. 552 (2012).
(Continued)

*Primary Examiner* — Ishrat I Sherali
(74) *Attorney, Agent, or Firm* — Schiff Hardin LLP

(57) ABSTRACT

In a method and computer for evaluating medical image data of an examination subject, a clinical marker of the examination subject is acquired that characterizes a status of the examination subject in relation to a physiological parameter, and a normal value range for the physiological parameter is ascertained that is matched to the status of the examination subject as a function of the clinical marker. Medical image data of the examination subject are acquired, and a value of the physiological parameter of the examination subject is determined using the medical image data. This value is compared with the normal value range matched to the status of the examination subject, and the result of the comparison is provided as an output.

13 Claims, 2 Drawing Sheets

(51) Int. Cl.
    *A61B 5/055*     (2006.01)
    *A61B 6/03*     (2006.01)
    *A61B 8/00*     (2006.01)
    *G06T 7/00*     (2017.01)

(56) References Cited

U.S. PATENT DOCUMENTS

| | | | |
|---|---|---|---|
| 2006/0173663 A1* | 8/2006 | Langheier | G16H 50/20 703/11 |
| 2013/0129168 A1* | 5/2013 | Ross | G06T 7/0012 382/128 |
| 2015/0056721 A1* | 2/2015 | Siman | G01N 33/6896 436/501 |
| 2016/0203263 A1* | 7/2016 | Maier | G06F 19/321 705/2 |
| 2017/0145506 A1* | 5/2017 | Merchant-Borna | C12Q 1/6883 |

OTHER PUBLICATIONS

Thompson et al., "The ENIGMA Consortium: Large-Scale Collaborative Analyses of Neuroimaging and Genetic Data", Brain Imaging and Behavior, vol. 8, pp. 153-182 (2014).
Schmitter et al., "An evaluation of volume-based morphometry for prediction of mild cognitive impairment and Alzheimer's disease", NeuroImage: Clinical vol. 7, pp. 7-17 (2015).
Regalado, "Genes influence the size of brain structures," Technology Review (2015).

\* cited by examiner

METHOD, COMPUTER AND IMAGING APPARATUS FOR EVALUATING MEDICAL IMAGE DATA OF AN EXAMINATION SUBJECT

BACKGROUND OF THE INVENTION

Field of the Invention

The invention concerns a method for evaluating medical image data of an examination subject, as well as an evaluation computer, a medical imaging apparatus and a non-transitory data storage medium for implementing such a method.

Description of the Prior Art

Typically, medical image data are recorded by medical imaging systems and can represent anatomical structures and/or functional processes of the body of an examination subject. An approach for evaluating the medical image data is known in which the medical image data acquired from the examination subject are compared with reference image data of the same examination subject in a healthy state, i.e. in particular in a state prior to the onset of disease symptoms. However, the presence of the reference image data is necessary for this approach, and such data are not available in most cases.

A further possibility for evaluating the medical image data is known that can be implemented independently of the presence of reference image data. The medical image data acquired from the examination subject are evaluated by semiautomatic or automatic analysis tools. This enables a value of a physiological parameter to be determined on the basis of the medical image data acquired from the examination subject. The thus determined value of the physiological parameter can be compared with a normal value range. In this case the normal value range typically indicates percentiles within which the value of the physiological parameter can be considered normal or non-suspect. A value of the physiological parameter outside of the normal value range, on the other hand, can point to a suspect situation or to the presence of a disease in the examination subject.

SUMMARY OF THE INVENTION

An object of the invention is to enable an evaluation of medical image data that is specifically matched to the examination subject.

The method according to the invention for evaluating medical image data of an examination subject includes the following method steps.

A clinical marker of the examination subject is acquired that characterizes a status of the examination subject in relation to a physiological parameter, and an electronic input represented by the clinical marker is provided to a computer. A normal value range for the physiological parameter is determined in the computer that is matched to the status of the examination subject dependent on the clinical marker. Medical image data are acquired from the examination subject, and also provided to the computer. A value of the physiological parameter of the examination subject is determined in the computer using the medical image data. The value of the physiological parameter is compared in the computer with the normal value range matched to the status of the examination subject, and the computer provides an electronic output representing a result of the comparison.

The examination subject can be a patient, a healthy test subject or an animal.

The acquisition of the clinical marker can be measuring the clinical marker or loading an already measured clinical marker of the examination subject from a database. Suitable parameters acquired from the examination subject that characterize the status of the examination subject in relation to the physiological parameter can serve as a clinical marker. In typical cases the clinical marker is not acquired in this instance by medical imaging of the examination subject. Rather, genetic data acquired from the examination subject, i.e. genetic variants or gene sequences of the examination subject, can be used as the clinical marker, as described in more detail below. It is also conceivable for a blood value of the examination subject to be determined as the clinical marker, as described in more detail below. The clinical marker of the examination subject can also be determined during a physical examination of the examination subject, by a specialist for example. It is also conceivable that the presence of a particular disease in the examination subject is used as the clinical marker, for example by retrieving a diagnosis associated with the examination subject from a hospital information system. Further examples of clinical markers that can be acquired from the examination subject that are considered suitable by those skilled in the art are also possible. A suitable method, for example a molecular diagnostic method or a blood analysis method, can be used for acquiring the clinical marker. Alternatively or in addition, a body fluid analysis method can be used for acquiring the clinical marker, such as a method for analyzing blood, urine, cerebrospinal fluid (liquor cerebrospinalis), etc. In specific application cases, an in-vitro diagnostic method can also be used alternatively or additionally for acquiring the clinical marker, in which case samples originating from the body are examined.

The physiological parameter is characterized by being quantifiable by medical imaging. This means that a value of the physiological parameter assigned to the examination subject, in particular a physical unit within a scale, is determinable using medical image data acquired from the examination subject. The physiological parameter can have a relation to an anatomical or a functional state of the body of the examination subject. It is conceivable for example that a size or volume of an organ structure of the examination subject is determined as the physiological parameter. A vessel density in a body region of the examination subject can also be determined as a physiological parameter. Also conceivable as physiological parameters are tissue parameters that can be determined by quantitative magnetic resonance imaging, such as averaged T1 values, T2 values, diffusion coefficients, etc. The physiological parameters cited here are only examples, so other physiological parameters deemed suitable by those skilled in the art are also conceivable.

The value of the physiological parameter determined by medical imaging can thus represent the measured value of the physiological parameter with respect to the specific examination subject. The measured value of the physiological parameter is in this case ascertained on the basis of the medical image data acquired from the examination subject. The acquisition of the medical image data can be recording the medical image data by operation of a medical imaging apparatus. Alternatively, the acquisition of the medical image data can be loading already recorded medical image data from an image database. Determining the value of the physiological parameter of the examination subject using the medical image data can in this case be a manual or semi-automatic or automatic evaluation of the medical image data. In certain application cases, determining the value of the physiological parameter can entail a morphometric analysis of the medical image data, wherein a size or volume of an organ structure is determined. Generally, the calculation of the value of the physiological parameter using the medical image data can be carried out by a method that is known to those skilled in the art and is suitable for determining the physiological parameter.

The clinical marker acquired from the examination subject characterizes a status of the examination subject that stands in relation to the physiological parameter of the examination subject in such a way that the status has an effect on an expected value of the physiological parameter. The status of the examination subject can in this way have an influence on normative values or a normal value range for the value of the physiological parameter. In particular, the presence of a certain status of the examination subject, which can be identified by the clinical marker, can be a pointer to a physiological deviation of the value of the physiological parameter from normal values. For example, the thus identified status can point to an abnormal development of the body or of an organ structure of the examination subject. Such an abnormal development of the body or the organ structure of the examination subject is in this case due to the physiological status of the examination subject and in principle does not point to a disease. Thus, for example, the status of the examination subject determined by the clinical marker can be the presence of a particular gene variant of the examination subject. It is also conceivable for a level of a blood value that can characterize the status of the examination subject to be determined as the clinical marker on the basis of a blood analysis.

Due to the relationship of the clinical marker determined from the examination subject or, as the case may be, the associated status of the examination subject with the expected values of the physiological parameter, the normal value range for the physiological parameter that is matched to the status of the examination subject can be ascertained as a function of the clinical marker. The normal value range matched to the status of the examination subject can be established by an algorithm that, as input parameters, has a generic normal value range or standard normal value range and the status of the examination subject or the clinical marker acquired from the examination subject. An adapted normal value range matched to the examination subject can then be present as the output parameter of the algorithm. In this way, an extent and/or a location of the normal value range can be chosen individually for the examination subject as a function of the clinical marker acquired from the examination subject.

Instead of the standard normal value range being adapted on the basis of the clinical marker, the clinical marker acquired from the examination subject can be used as a selection parameter for selecting a suitable look-up or reference table for the normal value range matched to the status of the examination subject. Thus, for example, a reference table expanded by the status of the examination subject can be used for comparing the value of the physiological parameter with the normal value range matched to the status of the examination subject.

The value of the physiological parameter determined from the medical image data, i.e. the measured value of the physiological parameter, is then compared with the normal value range matched to the status of the examination subject, and not with the standard normal value range. A result of the comparison can reflect whether the measured value of the physiological parameter lies within the normal value range matched to the status of the examination subject or not. The result of the comparison can furthermore include statistical data or a classification based on the measured value of the physiological parameter and the normal value range matched to the status of the examination subject. Adjusting the standard normal value range on the basis of the clinical marker can in this case lead to a situation where a measured value of the physiological parameter, though lying within the generic normal value range, is not in the normal value range matched to the status of the examination subject. In this way a potentially pathological deviation in the value of the physiological parameter determined from the medical image data can be ascertained individually for the examination subject. Needless to say, the reverse case, in which the measured value of the physiological parameter lies in the normal value range matched to the status of the examination subject, though not in the standard normal value range, is also conceivable. Providing the result of the comparison can entail emitting the result of the comparison to an output unit (monitor) and/or storing the result of the comparison in a database.

The inventive approach is accordingly based on the combined use of medical imaging and diagnostic methods, for example molecular diagnostics, which serve to acquire the clinical marker of the examination subject. With the inventive approach it is possible to determine normal value ranges for the physiological parameter that are individually matched to the examination subject. Thus, it is possible to increase the sensitivity of an evaluation of the medical image data in relation to the value of the physiological parameter determined on the basis of the medical image data. The diagnostic value of the measured value of the physiological parameter can also be increased in this way.

In an embodiment, genetic data of the examination subject are acquired as the clinical marker. The genetic data can be acquired by a molecular diagnostic method known to those skilled in the art. Genetic data relates to the hereditary characteristics specific to the examination subject, for example a part of a DNA sequence of the examination subject or a part of the genetic fingerprint of the examination subject. The genetic data of the examination subject that are acquired have an influence on the physiological parameter that is quantified on the basis of the medical image data. The genetic data actually acquired from the examination subject can therefore depend on the clinical problem. The status of the examination subject that is characterized by the genetic data can then be the presence of a gene variant in the examination subject or a change in a DNA section in a region between genes (intergenic variant). The status of the examination subject identified in this way on the basis of the genetic data can then be used to establish the normal value range for the physiological parameter that is matched to the status of the examination subject. This approach is based on the consideration that the genetic data of the examination subject can have an effect on a value range in which the values of the physiological parameter can be regarded as physiological and innocuous. In the case of an examination subject in which certain genetic data, for example a gene variant, is present, a measured value of the physiological parameter can point to the presence of a pathology, even though said measured value would be regarded as innocuous in relation to the standard normal value range for a larger patient population. Taking the genetic data into consideration in the adjustment of the normal value range can therefore lead to an increase in sensitivity in the assessment of the medical image data.

In another embodiment, genetic data are acquired that have an effect on a characteristic of an organ structure of the examination subject, wherein the physiological parameter reflects the characteristic of the organ structure. In this case the organ structure can be an organ of the examination subject, a delimited part of the examination subject, a group of organs of the examination subject, etc. The characteristic can in this case be a morphological or functional characteristic of the organ structure. The genetic data of the examination subject in this case has a physiological influence on the characteristic of the organ structure. The physiological parameter that reflects the characteristic of the organ structure must in this case be quantifiable on the basis of the medical image data.

In another embodiment, the characteristic of the organ structure be a size or volume of the organ structure. The size or volume of the organ structure can in this case be characterized particularly easily on the basis of the medical image data. The hippocampus of the examination subject is an example of such an organ structure. The volume or size of the hippocampus is influenced by gene variants of the examination subject, for example the intergenic variant rs7294919 according to the work by J. L. Stein et al.: "Identification of common variants associated with human hippocampal and intracranial volume", Nature Genetics, 44:552 (2012). Other examples that reveal a strong connection between genetic data and the volume of brain structures are contained in the work by P. M. Thompson et al.: "The ENIGMA Consortium: Large-Scale Collaborative Analyses of Neuroimaging and Genetic Data", Brain Imaging and Behavior, 8:153 (2014).

In another embodiment, the normal value range matched to the status of the examination subject is ascertained as a function of a gene variant identified in the genetic data of the examination subject. In a specific application case, a first normal value range and a second normal value range can be defined here, the first normal value range being used as a normal value range matched to the status of the examination subject if the examination subject does not have the gene variant and the second normal value range being used as a normal value range matched to the status of the examination subject if the examination subject has the gene variant. The first normal value range can in this case be the already mentioned generic normal value range, while the second normal value range has limits for the value of the physiological parameter that differ compared to the first normal value range. An evaluation of the medical image data that is advantageously matched to genetic characteristics of the examination subject can be conducted by of this approach.

In a further embodiment, a blood value of the examination subject is determined as the clinical marker. In this case the blood value can be determined by methods known to those skilled in the art, for example within a small or large blood count. In this case the blood value, for example, can characterize a concentration of blood cells, a quantity of dissolved substances in the blood of the examination subject or a concentration of certain proteins in the blood. The blood value of the examination subject that is measured has an influence on the physiological parameter that is quantified on the basis of the medical image data. It should be noted that even when the blood value is used as a clinical marker, the adjustments of the normal value range already described for the use of genetic data as a clinical marker can be carried out. In this way the normal value range matched to the status of the examination subject can advantageously be ascertained as a function of a level of the blood value of the examination subject. The other embodiment variants in relation to the genetic data as a clinical marker can likewise be applied analogously to the blood value as a clinical marker.

In another embodiment, a standard normal value range is provided for a group of comparable examination subjects, wherein the standard normal value range for ascertaining the normal value range matched to the status of the examination subject is adapted specifically for the examination subject as a function of the acquired clinical marker. The standard normal value range can be in particular a generic normal value range. This can be present, for example, in the form of a reference table or an atlas. The standard normal value range can indicate which values of the physiological parameter can be regarded as normal for a larger patient population. The standard normal value range is in this case in particular not matched individually to the examination subject. The standard normal value range can, however, be chosen as a function of certain parameters of the examination subject, such as the age and/or sex of the examination subject, for example. The adjustment of the standard normal value range taking the clinical marker into consideration can be a shifting of a lower limit value and/or an upper limit value of the standard normal value range. The standard normal value range can in this way represent a particularly advantageous starting point for determining the normal value range matched to the status of the examination subject.

In another embodiment, the physiological parameter reflects a characteristic of an organ structure of the examination subject, wherein the medical image data maps the organ structure, which means that the organ structure is localized at least partially, preferably completely, in a field of view or volume of interest recorded in the medical image data. With regard to the organ structure or the characteristic of the organ structure, reference is made to the description in any of the preceding paragraphs.

In another embodiment, determining the value of the physiological parameter is a segmentation of the organ structure in the medical image data. The segmentation of the organ structure can be accomplished using conventional methods known to those skilled in the art. For example, an atlas-based segmentation can be carried out that includes registering and adapting an atlas organ structure stored in an atlas to the organ structure mapped in the medical image data. In this way the segmentation of the organ structure can be an automatic or semiautomatic morphometric analysis. On the basis of the segmentation of the organ structure, the value of the physiological parameter that reflects the characteristic of the organ structure can be determined particularly advantageously matched to the organ structure.

In another embodiment, the organ structure is a substructure of the brain of the examination subject, and the characteristic of the organ structure is a volume of the substructure of the brain, and the determining of the value of the physiological parameter is determining the volume of the substructure of the brain on the basis of the medical image data. The substructure of the brain can be, for example, the hippocampus, a ventricle, the thalamus, gray or white brain matter, the amygdala, the cerebellum, etc. The volume of the substructure of the brain can offer a significant possibility for evaluating the medical image data, in particular with regard to neurological diseases or disorders of the examination subject. Thus, the volume of the substructure of the brain can be an early indicator of neurodegenerative diseases, such as Alzheimer's disease, for example, as described for example in the paper by D. Schmitter et al.: "An evaluation of volume-based morphometry for prediction of mild cognitive impairment and Alzheimer's disease", NeuroImage: Clinical 7:7 (2015). At the same time, the volume of the substructure of the brain can often be dependent on a genetic state of the examination subject which can be acquired as a clinical marker, such as described in the above-cited works by J. L. Stein or P. M. Thompson.

In another embodiment, a total intracranial volume is determined on the basis of the medical image data, and the determining of the value of the physiological parameter comprises determining the volume of the substructure of the brain which is normalized to the total intracranial volume. In this way the value of the physiological parameter does not describe the absolute volume of the substructure of the brain, but instead is a ratio of the volume of the substructure of the brain in relation to the total intracranial volume. In this way interfering dependencies of an actual total volume of the brain of the examination subject can be eliminated or reduced in the comparison of the volume of the substructure of the brain with the normal value range for the volume matched to the examination subject.

In another embodiment, the providing of the result of the comparison involves providing a two-dimensional or three-dimensional map that represents the value of the physiological parameter in relation to the normal value range matched to the status of the examination subject in a spatially resolved manner. In this way the user is provided with the result of the comparison not just by statistical values or characteristic data. Rather, the result of the comparison is presented in particular graphically on the two-dimensional or three-dimensional map. In this case the map can be displayed as an overlay to a visualization of the medical image data. The map can be a spatially resolved representation of the extent to which the physiological parameter lies inside or outside of the normal value range matched to the status of the examination subject. The value of the physiological parameter in relation to the normal value range matched to the status of the examination subject can be represented in the map in color-coded form. The physiological parameter can also reflect a characteristic of an organ structure of the patient, wherein the value of the physiological parameter in relation to the normal value range matched to the status of the patient is represented in the map in structure-based form for the organ structure, based on a segmentation of the organ structure. An especially graphic representation of the result of the comparison is possible by this approach. This approach is particularly beneficial in the representation of the deviation of a volume of a substructure of the brain of the examination subject from the adjusted normal value range.

The evaluation computer according to the invention has a first acquisition processor, an ascertainment processor, a second acquisition processor, a determination processor, a comparison processor, and an output interface. The evaluation computer is configured overall for performing the method according to the invention.

Thus, the evaluation computer is designed (programmed) to perform the inventive method for evaluating medical image data of an examination subject. The first acquisition processor is designed for acquiring a clinical marker of the examination subject that characterizes a status of the examination subject in relation to a physiological parameter. The ascertainment processor is designed for establishing a normal value range for the physiological parameter that is matched to the status of the examination subject as a function of the clinical marker. The second acquisition processor is designed for acquiring medical image data of the examination subject by operation of a medical imaging apparatus. The determination processor is designed for determining a value of the physiological parameter of the examination subject using the medical image data. The comparison processor is designed for comparing the value of the physiological parameter with the normal value range matched to the status of the examination subject. The output interface is designed for providing a result of the comparison as an electronic output signal.

The components of the evaluation computer, namely the first acquisition processor, ascertainment processor, second acquisition processor, determination unit, comparison processor and the output interface, can be for the most part in the form of software components. In principle, however, these components can also be realized in some instances, particularly when fast calculations are needed, in the form of software-assisted hardware components, for example FPGAs or the like. Equally, the required interfaces can be embodied as software interfaces, for example when it is simply a matter of importing data from other software components. They can, however, also be embodied as hardware-based interfaces that are controlled by suitable software. It is of course also conceivable for a number of the cited components to be implemented in combination in the form of a single software component or software-assisted hardware component.

The medical imaging apparatus according to the invention has an evaluation computer according to the invention. The evaluation computer can be designed to send control signals to the medical imaging apparatus and/or for receiving and/or processing control signals in order to perform the method according to the invention. The evaluation computer can be integrated into the medical imaging apparatus. The evaluation computer can also be installed separately from the medical imaging apparatus. The evaluation computer can be connected to the medical imaging apparatus. The medical image data can be acquired by a scanner of the medical imaging apparatus. The medical image data can then be transferred to the evaluation computer for further processing. The evaluation computer can then acquire the medical image data via the second acquisition processor for the purposes of the evaluation.

A non-transitory, computer-readable data storage medium according to the invention can be loaded directly into a memory of a programmable evaluation computer and has program code that causes the method according to the invention to be implemented when the program code is executed in the evaluation computer. This enables the method according to the invention to be carried out quickly and in an identically reproducible and robust manner. The computer must have the prerequisites for this, such as a random access memory, for example, a graphics card or a corresponding logic unit, so that the respective method steps can be performed efficiently. Examples of electronically readable data storage media are a DVD, a magnetic tape or a USB stick on which electronically readable control information, in particular software (cf. above), is stored. When the control information (software) is read from the data storage medium and stored in a controller and/or processor of the evaluation computer, all of the inventive embodiments of the method described can be performed.

The advantages of the inventive evaluation computer, the inventive medical imaging apparatus and the inventive storage medium essentially correspond to the advantages of the inventive method, as presented in detail above. Features, advantages or alternative embodiments mentioned in this context are applicable to the other aspects of the invention.

The functional features of the method are embodied as corresponding object-related modules, in particular by hardware modules.

DESCRIPTION OF THE PREFERRED EMBODIMENTS

Figure 1:
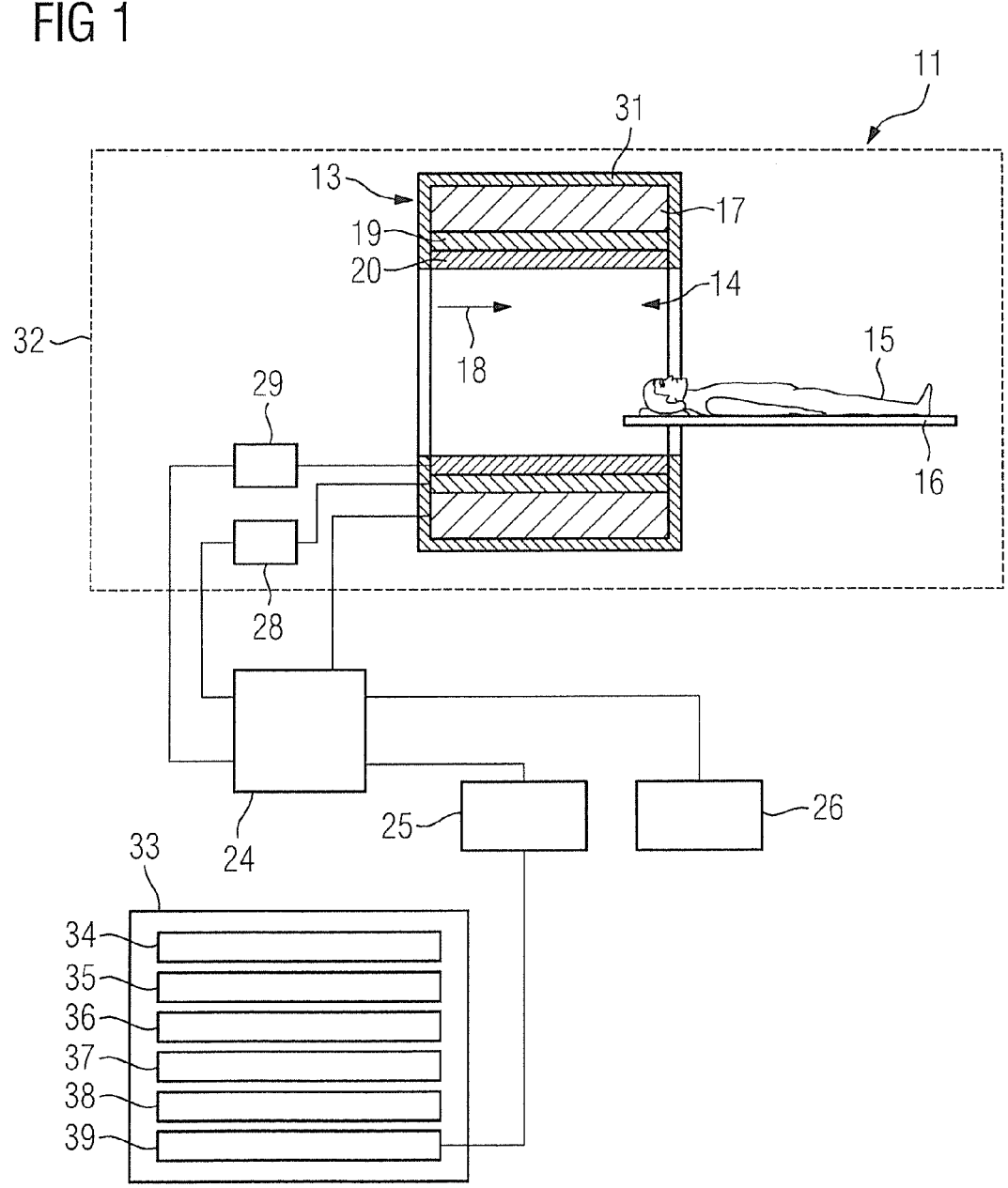
FIG. 1 is a schematic illustration of a medical imaging apparatus according to the invention having an evaluation computer according to the invention.

FIG. 1 shows a medical imaging apparatus according to the invention having an evaluation computer 33 according to the invention, in a schematic view.

The medical imaging apparatus can be, for example, a magnetic resonance apparatus, a single-photon emission tomography (SPECT) apparatus, a positron emission tomography (PET) apparatus, a computed tomography (CT) apparatus, an ultrasound apparatus, an X-ray machine or a C-arm apparatus. Also possible in this context are combined medical imaging apparatuses formed by an arbitrary combination of a number of the cited imaging modalities. In the case shown, the medical imaging apparatus is, as an example, a magnetic resonance apparatus 11.

The magnetic resonance apparatus has a scanner 13 having a basic field magnet 17 for generating a strong and constant basic magnetic field 18. The scanner 13 has a cylinder-shaped patient receiving zone 14 for accommodating an examination subject 15, in the present case a patient, the patient receiving zone 14 being cylindrically enclosed by the scanner 13 in the circumferential direction. The patient 15 can be introduced into the patient receiving zone 14 by a patient support 16 of the magnetic resonance apparatus 11. For this purpose, the patient support 16 has a patient table that is movable inside the scanner 13. The scanner 13 is shielded externally by a housing enclosure 31.

The scanner 13 additionally has a gradient coil arrangement 19 for generating magnetic field gradients that are used for spatial encoding during an imaging session. The gradient coil arrangement 19 is driven by a gradient controller 28. The scanner 13 furthermore has a radio-frequency antenna 20, which in the case shown is a body coil permanently integrated in the scanner 13, and a radio-frequency antenna controller 29. The radio-frequency antenna 20 is driven by the radio-frequency antenna controller 29 so as to radiate radio-frequency magnetic resonance sequences into an examination chamber that is substantially formed by the patient receiving zone 14. The radiated radio-frequency sequence causes nuclear spins of certain atoms in the examination subject 15 to be tilted (flipped) from the equilibrium state defined by the field lines of the basic magnetic field 18. As the excited nuclear spins relax, they emit radio-frequency signals, called magnetic resonance signals. The radio-frequency antenna 20 is furthermore designed to receive magnetic resonance signals, such as with a local coil thereof (not shown).

The magnetic resonance apparatus 11 has a computer 24 for controlling the basic field magnet 17, the gradient controller 28 and the radio-frequency antenna controller 29. The computer 24 is responsible for the centralized control of the magnetic resonance apparatus 11, such as performing a predetermined imaging gradient echo sequence. Control information such as imaging parameters, as well as reconstructed magnetic resonance images can be provided for a user on an output device 25, in the present case a display monitor, of the magnetic resonance apparatus 11. The magnetic resonance apparatus 11 additionally has an input device 26 via which information and/or parameters can be entered by a user during a measurement procedure. The computer 24 can include the gradient controller 28 and/or the radio-frequency antenna controller 29 and/or the display device 25 and/or the input device 26.

The illustrated magnetic resonance apparatus 11 can of course have further components that are ordinarily present in magnetic resonance apparatuses. The general principle of operation of a magnetic resonance apparatus is known to those skilled in the art, so a more detailed description is not necessary herein.

The illustrated evaluation computer 33 has a first acquisition processor 34, an ascertainment processor 35, a second acquisition processor 36, a determination processor 37, a comparison processor 38, and an output interface 39.

The second acquisition processor 36 of the evaluation computer 33 can receive medical image data which have been acquired by operation of the scanner 13, from the computer 24 of the magnetic resonance apparatus 11. For this purpose the second acquisition processor 36 is connected to the computer 24 of the magnetic resonance apparatus 11 in order to enable an exchange of data (serving as an input interface). In this arrangement, the output interface 39 is connected to the display device 25 of the magnetic resonance apparatus 11 so that the result of the comparison can be displayed. The magnetic resonance apparatus 11 is accordingly configured together with the evaluation computer 33 for performing the inventive method for evaluating medical image data.

Alternatively to the illustrated arrangement, the evaluation computer 33 can be configured for performing the inventive method for evaluating medical image data on a standalone basis. To that end, the second acquisition processor 36 of the evaluation computer 33 will typically load image data from a database and/or retrieve image data from a connected medical imaging apparatus.

Figure 2:
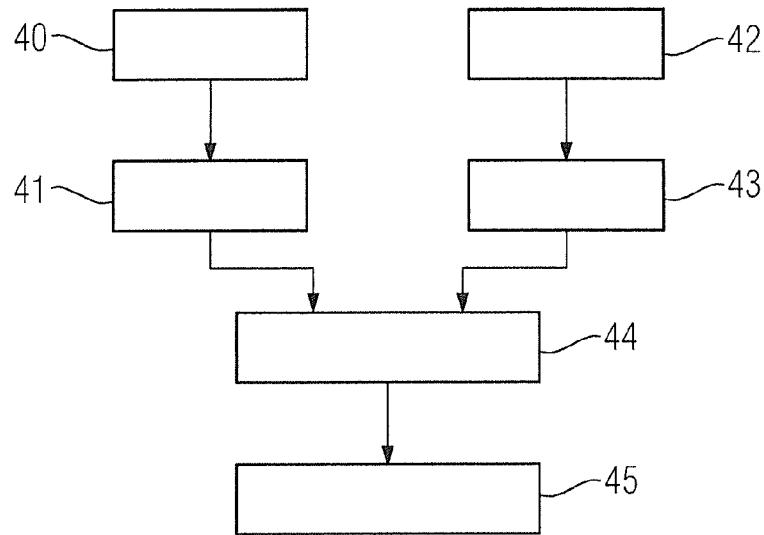
FIG. 2 is a flowchart of a first embodiment of the method according to the invention.

FIG. 2 shows a flowchart of a first embodiment of the inventive method for evaluating medical image data.

In a first method step 40, a clinical marker of the examination subject is acquired by means of the first acquisition processor 34, wherein the clinical marker characterizes a status of the examination subject in relation to a physiological parameter.

In a further method step 41, a normal value range for the physiological parameter that is matched to the status of the examination subject is ascertained as a function of the clinical marker by the ascertainment processor 35.

In a further method step 42, medical image data of the examination subject is acquired by the second acquisition processor 36.

In a further method step 43, a value of the physiological parameter of the examination subject is determined by means of the determination processor 37 using the medical image data.

In a further method step 44, the value of the physiological parameter is compared with the normal value range matched to the status of the examination subject by the comparison processor 38.

In a further method step 45, a result of the comparison is provided as an output by the output interface 39.

Figure 3:
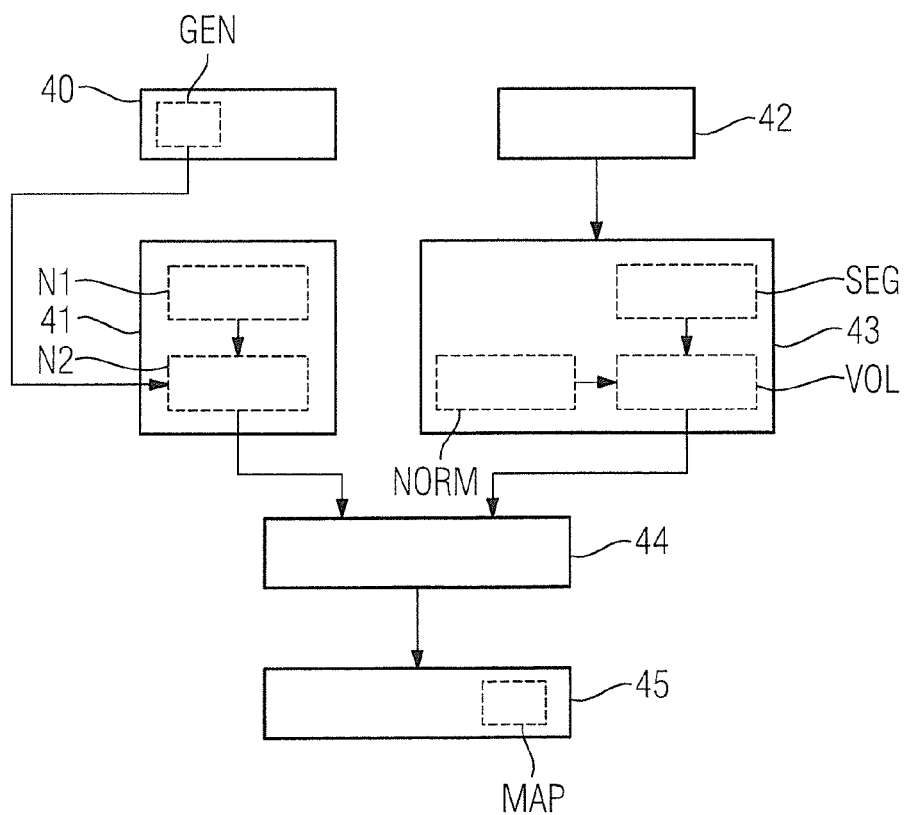
FIG. 3 is a flowchart of a second embodiment of the method according to the invention.

FIG. 3 shows a flowchart of a second embodiment of the inventive method for evaluating medical image data.

The following description limits itself essentially to the differences compared to the exemplary embodiment in FIG. 2, with reference being made to the description of the exemplary embodiment in FIG. 2 in respect of method steps that remain the same. Method steps that remain substantially the same are labeled consistently with the same reference numerals.

The embodiment of the inventive method shown in FIG. 3 essentially includes the method steps 40, 41, 42, 43, 44, 45 of the first embodiment of the inventive method according to FIG. 2. The embodiment of the inventive method shown in FIG. 3 has additional method steps and substeps. An alternative method execution sequence to FIG. 3 that includes only some of the additional method steps and/or substeps shown in FIG. 3 is also conceivable. An alternative method execution sequence to FIG. 3 can of course also include additional method steps and/or substeps.

The embodiment of the inventive method described in FIG. 3 is aimed at an evaluation of medical image data acquired from the brain of an examination subject. For almost every neurological disease, it is essential to establish the diagnosis at an early stage in order to ensure a timely commencement of treatment. In certain neurological disorders, such as Alzheimer's disease, the symptoms progress with anatomical changes in the brain. Typically, as with Alzheimer's disease for example, specific regions in the brain are affected by atrophy. As described in the cited work by D. Schmitter et al., the volume of substructures of the brain, for example, can have an influence on the prognosis of cognitive impairments and Alzheimer's disease. A volume of a substructure of the brain ascertained by medical image data can therefore be compared with normal value ranges for said volume in order to identify a potentially suspect state of the substructure of the brain.

However, there can also be other factors which influence morphological characteristics of organs of the examination subject, of the brain for example. Different people's brains develop differently, particularly under the influence of a genetic background. Accordingly, the volume of substructures of the brain can also deviate from an age-related average purely for physiological reasons. Correlations between a genetic background of the examination subject and volumes of substructures of the brain are described for example in the cited papers by P. M. Thompson et al. and J. L. Stein et al. By a combination of medical imaging and molecular diagnostics, the approach described in FIG. 3 enables normal value ranges for the volume of substructures of the brain to be adjusted and thereby permits an increased sensitivity in the evaluation of the medical image data.

According to FIG. 3, the first method step 40 has for this purpose a substep GEN in which genetic data of the examination subject is acquired as a clinical marker. In this case, such genetic data can be acquired in substep GEN which has an influence on a characteristic of an organ structure of the examination subject, wherein the physiological parameter reflects the characteristic of the organ structure. The characteristic of the organ structure can in this case comprise a size or a volume of the organ structure.

In order to ascertain Alzheimer's disease or precursor stages of Alzheimer's disease, such as a mild cognitive impairment for example, genetic data which influences a volume of the hippocampus of the examination subject is of interest, for example. In substep GEN, for example, it can be identified in the genetic data whether the examination subject is affected by the intergenic variant rs7294919 which, according to the already cited work by J. L. Stein et al., has an influence on the hippocampal volume.

According to FIG. 3, the further method step 41, the ascertaining of a normal value range for the physiological parameter that is matched to the status of the examination subject as a function of the clinical marker, comprises a first substep N1 and a second substep N2.

In the first substep N1, a standard normal value range for a cohort of examination subjects is provided. In the described case of the evaluation of the volume of the hippocampus in relation to Alzheimer's disease, it can be assumed for example that a 54-year old patient is to be examined. According to this age, it can be assumed by way of example that 90 percent of the healthy population have a hippocampal volume between 80 and 100. This value range can be applied as the standard normal value range for the volume of the hippocampus. It is to be understood that the cited numeric values are provided only for illustration purposes and are to be regarded as hypothetical.

In the second substep N2, the standard normal value range is now adjusted specifically for the examination subject in order to ascertain the normal value range matched to the status of the examination subject as a function of the acquired clinical marker. For this purpose the genetic data acquired as a clinical marker can be translated for example by means of a reference table into corresponding volume information. For example, the presence of the mentioned intergenic variant rs7294919 can lead to an increase in an expected normal volume of the hippocampus in comparison with the population average. It can be assumed for example that the intergenic variant rs7294919 has been identified in the examination subject. Said intergenic variant indicates that the hippocampal volume of this individual is approx. 10 percent greater than the population average. It is to be understood that this deviation also is to be regarded as by way of example only and is cited with a hypothetical value, whereas in the real-world case smaller deviations will typically be present. Based on this knowledge, the standard normal value range can now be adjusted individually for the examination subject. The adjustment can in this case be an increase in the limits of the standard normal value range by 10 percent. The lower limit of the standard normal value range is therefore raised from 80 to 88, while the upper limit of the standard normal value range is raised from 100 to 110. Due to the presence of the intergenic variant rs7294919, the normal value range matched to the status of the examination subject has accordingly been established in substep N2 as extending from 88 to 110 for the volume of the hippocampus.

In the present exemplary embodiment, the medical image data acquired in the further method step 42 can be magnetic resonance image data acquired by a magnetic resonance apparatus, since such data allow a particularly good delimitation of the hippocampus in relation to other brain structures. Particularly advantageously, a T1-weighted magnetic resonance sequence, for example a three-dimensional rapid gradient echo acquisition with magnetization preparation (3D MP-RAGE sequence), can be used for acquiring the medical image data. The resolution of the medical image data can be isotropic and amount to 1 mm, for example. The medical image data map the organ structure of interest, i.e. the hippocampus in the present case.

In the further method step 43, the value of the physiological parameter is now ascertained using the medical image data. According to FIG. 3, the value of the physiological parameter is intended to characterize the actual hippocampal volume of the examination subject as a characteristic of the hippocampus.

For this purpose, the further method step 43 has a first substep SEG in which a segmentation of the organ structure, i.e. of the hippocampus in the specific application case, is carried out in the medical image data. The volume of the substructure of the brain can then be quantified in a substep VOL of the further method step 43 by means of known morphometric methods on the basis of the segmentation of the substructure of the brain. If it is assumed that a volume of 82 is ascertained for the hippocampus on the basis of the medical image data, the hippocampal volume can accordingly be ascertained in this way. In many application cases it can be advantageous to determine a total intracranial volume in a further substep NORM on the basis of the medical image data and to perform the determination of the volume of the substructure of the brain normalized to the total intracranial volume.

In the further method step 44, the volume of the hippocampus determined in substep VOL of the further method step 43 can now be compared with the normal value range for the volume of the hippocampus matched to the status of the examination subject ascertained in substep N2 of the further method step 42. The hippocampal volume of 82 actually ascertained for the examination subject on the basis of the medical image data lies outside of the normal value range matched to the status of the examination subject, which possesses the lower limit 88. In this way a presence of pathological changes to the hippocampus of the examination subject can possibly be inferred. If the hippocampal volume of 82 had been compared with the standard normal value range of 80-100, no standard deviation would have been identified. This example can therefore illustrate how the method according to the invention leads to an increase in sensitivity in the evaluation of the medical image data.

Providing the result of the comparison in the further method step 45 can be providing a two-dimensional or three-dimensional map MAP representing the value of the physiological parameter in relation to the normal value range matched to the status of the examination subject in a spatially resolved manner. According to FIG. 3, the hippocampus can for example be displayed conspicuously in color in the medical image data displayed for a user, since the hippocampal volume established for the examination subject lies outside of the normal value range for the hippocampal volume matched to the status of the examination subject.

The method shown in FIG. 3 is intended only to describe an exemplary possibility for the approach according to the invention. It is to be understood that other versions considered beneficial by those skilled in the art are also conceivable. For example, a blood value can be acquired as a clinical marker instead of genetic data. The medical image data can also be acquired, for example, from a different body region than the brain of the examination subject. Other characteristics of the organ structures than the volume of the organ structure can also be examined. All numeric values cited in FIG. 3 are of course provided for illustration purposes only.

The method steps of the inventive method depicted in FIGS. 2-3 are performed by the evaluation unit. For this purpose the evaluation unit comprises requisite software and/or computer programs which are stored in a memory unit of the computing unit. The software and/or computer programs comprise program means which are configured for performing the inventive method when the computer program and/or the software is executed in the evaluation unit by means of a processor unit of the evaluation unit.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for evaluating medical image data obtained from an examination subject, comprising:
    providing an electronic input to a computer that designates a clinical marker of the examination subject that characterizes a status of the examination subject in relation to a physiological parameter, said clinical marking having an influence on a characteristic of an organ structure of the examination subject, and said physiological parameter being a characteristic of said organ structure;
    in said computer, ascertaining a normal value range for said physiological parameter that is matched to the status of the examination subject as characterized by the clinical marker;
    providing medical image data of the examination subject to the computer;
    in said computer, analyzing said medical image data in order to determine a value of the physiological parameter of the examination subject from the medical image data, said value being of a size of the organ structure and a volume of the organ structure;
    in said computer, comparing the determined value of the physiological parameter with the normal value range matched to the status of the examination subject, and thereby obtaining a comparison result; and
    making an electronic signal representing said comparison result available at an output of the computer.

2. A method as claimed in claim 1 comprising providing genetic data of the examination subject to the computer as said clinical marker.

3. A method as claimed in claim 1 comprising matching said normal value range to the status of the examination subject as a function of a gene variant identified in the genetic data of the examination subject.

4. A method as claimed in claim 1 comprising providing a blood value of the examination subject as said clinical marker.

5. A method as claimed in claim 1 comprising providing said computer with a standard normal value range for a population of examination subjects comparable to said examination subject, and adjusting said standard normal value range in said computer specifically for said examination subject as a function of the clinical marker in order to ascertain said normal value range matched to the status of the examination subject.

6. A method as claimed in claim 1 wherein said medical image data map said organ structure.

7. A method as claimed in claim 6 comprising determining said value of the physiological parameter by implementing a segmentation of said organ structure in the medical image data.

8. A method as claimed in claim 6 wherein said organ structure is a substructure of the brain of the examination subject, and wherein said characteristic of the organ structure is a volume of said substructure of the brain, and comprising determining the value of the physiological parameter by determining a volume of the substructure of the brain from said medical image data.

9. A method as claimed in claim 8 comprising determining a total intracranial volume of the examination subject from said medical image data, and determining said value of the physiological parameter by determining a volume of the substructure of the brain that is normalized to said total intracranial volume.

10. A method as claimed in claim 1 comprising providing said result as an electronic signal from the computer representing a spatially resolved two-dimensional map or a spatially resolved three-dimensional map of the value of the physiological parameter in relation to the normal value range matched to the status of the examination subject.

11. An evaluation computer comprising:
an input interface that receives an electronic input that designates a clinical marker of the examination subject that characterizes a status of the examination subject in relation to a physiological parameter, said clinical marking having an influence on a characteristic of an organ structure of the examination subject, and said physiological parameter being a characteristic of said organ structure;
a processor configured to ascertain a normal value range for said physiological parameter that is matched to the status of the examination subject as characterized by the clinical marker;
said input interface also receiving medical image data of the examination subject;
said processor being configured to analyze said medical image data in order to determine a value of the physiological parameter of the examination subject from the medical image data, said value being of a size of the organ structure and a volume of the organ structure;
said processor being configured to compare the determined value of the physiological parameter with the normal value range matched to the status of the examination subject, and thereby obtain a comparison result; and
said processor being configured to make an electronic signal representing said comparison result available at an output interface.

12. A medical imaging apparatus comprising:
a medical image data scanner;
a computer having an input interface that receives an electronic input to a computer that designates a clinical marker of the examination subject that characterizes a status of the examination subject in relation to a physiological parameter, said clinical marking having an influence on a characteristic of an organ structure of the examination subject, and said physiological parameter being a characteristic of said organ structure;
said computer being configured to ascertain a normal value range for said physiological parameter that is matched to the status of the examination subject as characterized by the clinical marker;
said computer also receiving, via said input interface, medical image data of the examination subject from the scanner;
said computer being configured to analyze said medical image data in order to determine a value of the physiological parameter of the examination subject using the medical image data, said value being of a size of the organ structure and a volume of the organ structure;
said computer being configured to compare the determined value of the physiological parameter with the normal value range matched to the status of the examination subject, and thereby obtain a comparison result; and
said computer being configured to make an electronic signal representing said comparison result available at an output of the computer.

13. A non-transitory, computer-readable data storage medium encoded with programming instructions, said storage medium being loaded into an evaluation computer of a medical imaging system, said programming instructions causing said evaluation computer to:
receive an electronic input that designates a clinical marker of the examination subject that characterizes a status of the examination subject in relation to a physiological parameter, said clinical marking having an influence on a characteristic of an organ structure of the examination subject, and said physiological parameter being a characteristic of said organ structure;
ascertain a normal value range for said physiological parameter that is matched to the status of the examination subject as characterized by the clinical marker;
receive medical image data of the examination subject to the computer;
analyze said medical image data in order to determine a value of the physiological parameter of the examination subject from the medical image data, said value being of a size of the organ structure and a volume of the organ structure;
compare the determined value of the physiological parameter with the normal value range matched to the status of the examination subject, and thereby obtain a comparison result; and
make an electronic signal representing said comparison result available at an output of the computer.

* * * * *